United States Patent [19]
Hale

[11] Patent Number: 6,016,713
[45] Date of Patent: Jan. 25, 2000

[54] SOIL SAMPLING "ON THE FLY"

[75] Inventor: George Hale, Naperville, Ill.

[73] Assignee: Case Corporation, Racine, Wis.

[21] Appl. No.: 09/124,595

[22] Filed: Jul. 29, 1998

[51] Int. Cl.$^7$ .................................................. G01N 1/08
[52] U.S. Cl. ........................................................ 73/864.45
[58] Field of Search ........................... 73/864.44, 864.45, 73/864.31, 864.81; 175/20, 58

[56]           References Cited

U.S. PATENT DOCUMENTS

| | | | |
|---|---|---|---|
| 3,224,512 | 12/1965 | Alexander | 73/864.45 |
| 5,220,876 | 6/1993 | Monson et al. | 111/130 |
| 5,394,949 | 3/1995 | Wright et al. | 175/20 |
| 5,461,229 | 10/1995 | Sauter et al. | . |
| 5,467,271 | 11/1995 | Abel et al. | 364/420 |
| 5,519,609 | 5/1996 | Kuchenrither et al. | 364/420 |
| 5,668,719 | 9/1997 | Bobrov et al. | 364/420 |
| 5,741,983 | 4/1998 | Skotnikov et al. | 73/864.44 |

OTHER PUBLICATIONS

Case Corp. Brochure No. AE–253018, "Case IH AFS Soil Samplers", 1997.
D. E. McGrath and A. Skotnikov, 1994, "Automated Systems to Optimize Productive Capacity of a Field for a Given Crop", *Computers in Agrigulture*, pp. 397–402; ASAE, 2950 Niles Rd., St. Joseph MI 49085.
Craig Kvien, Deborah Waters and Lynn Usery, Dec. 1995, "Farming in the Information Age", *Precision Farming*, pp. 10–19.
John Colburn, Dec. 31, 1986, "R&D On A Fertilizer Sensor And Control System", Phase I Report.
John E. Sawyer and Ron Milby, "Realities Of Providing Site–Specific Serivces To Customers", pp. 81–89.

*Primary Examiner*—Robert Raevis
*Attorney, Agent, or Firm*—Foley & Lardner

[57]            ABSTRACT

A site-specific precision farming system for acquiring soil samples from a field of land using a vehicle remaining in the operative motion normal to a field or crop operation being performed simultaneously is disclosed. The system includes a tractor, harvester, or other agricultural vehicle provided with an implement or other device appropriate to the operation being simultaneously performed; a soil sample acquiring device movable with respect to the vehicle such that the device is substantially stationary with respect to the soil while it acquires a sample; a locational identification system; a device for inserting each soil sample into an individual container and for marking the sample site locational identification thereon as alphanumeric indicia or as a barcode; and an on-board computer for control of the above processes. The vehicle may be provided with soil analysis equipment for real-time soil sample analysis or with sensors for other soil or crop parameters, and the computer may then log the resulting site-specific data correlated with the corresponding locational data to a portable memory device for removal to an off-site computer for data archiving and for generation of a prescriptive map. These data may instead be communicated to the off-site computer in real time, so that the off-site computer may function as a host computer monitoring and controlling a plurality of vehicles concurrently.

30 Claims, 8 Drawing Sheets

| DATA POINT | LOCATION | | | SOIL ANALYSIS | | |
|---|---|---|---|---|---|---|
| | LONGITUDE | LATITUDE | ALTITUDE, FT. ABOVE S.L. | P,ppm | K,ppm | pH |
| ... | ... | ... | ... | ... | ... | ... |
| 699 | −88.7291520 | 39.0710720 | 770 | 25 | 120 | 6.9 |
| 700 | −88.7291140 | 39.0710720 | 771 | 24 | 119 | 6.9 |
| 701 | −88.7290720 | 39.0710740 | 669 | 24 | 121 | 7.0 |
| ... | ... | ... | ... | ... | ... | ... |

SOIL SAMPLING "ON THE FLY"

FIELD OF THE INVENTION

The present invention relates to the acquiring of soil samples from an agricultural field for analysis. In particular, the invention relates to the site-specific acquisition of soil samples using a vehicle moving over a field.

BACKGROUND OF THE INVENTION

Until recently crop farm management has had little choice but to assume that fields are essentially homogeneous across their entire areas and has had to apply farming inputs (e.g., tillage techniques and extent, application of fertilizers and herbicides, and other working of soil and crops) at uniform rates over an entire field or set of fields. Recent technological developments within the agricultural community, however, now allow crop production to be optimized by learning and responding to spatial variations in soil conditions, as well as in other properties, that commonly exist within any given farming field. By varying the farm inputs applied to a field to compensate for local variations or anomalies within the field, a farmer can optimize crop yield and quality by providing the amount of input needed at a specific site. An additional benefit is reduction of potential environmental damage or degradation due to, for example, erosion, pesticides, or herbicides. This management technique has become known as precision, site-specific, prescriptive, or spatially-variable farming.

Precision farming requires the gathering and processing of data relating to site-specific characteristics of a field. These data may be loaded in a first data base, such as a geographic information system (GIS) program, and used to generate a prescriptive map. The prescriptive map may be a second data base defining a set of farming inputs or other operations to be performed spatially variably in response to the spatial variations found in the measured data of the first data base. While crop data are useful information for this purpose, they are essentially an end effect and the more causal relationship of site-specific soil analysis data are therefore of great importance. Generally, such data are obtained from analyses of multitudinous soil samples gathered from a field in, typically, a grid pattern.

There are many variations in combinations of procedures in which samples may be acquired, locationally identified, and analyzed. Various procedures may also be used to report or log analysis data, and these data may be used in some way to cause various portions of a field to produce in a more nearly uniform manner than if the field were treated with unvarying inputs as though it were homogeneous. The discussion below does not describe all such possible combinations, and is intended only to illustrate some which are representative.

Methods of obtaining discrete, site-specific soil samples have ranged in the prior art from a man walking into a field carrying a shovel and a pail to take at most a few samples, to a mobile probe or augur system mounted on an off-road vehicle and provided with a device to place each sample into a separate container. Heretofore, none have related to the obtaining of soil samples from a moving vehicle; that is, in the prior art, if the sampling device is vehicle-mounted the vehicle must come to a stop and remain stopped while the sample is acquired. Since generation of a prescriptive map in precision farming requires the gathering of many soil samples to discover and adequately delineate variations within a field, the work vehicle has to make many such stops. Although the costs of labor, fuel, and vehicle amortization and maintenance make a separately performed traversing of a field for the purpose of obtaining a multitude of soil samples a costly operation, it has not heretofore been practical to eliminate or reduce that cost by combining such a soil sampling operation with another farming operation, such as tilling or harvesting, because the frequent stops required would unduly interfere with performance of the approximately constant-speed farming operation. As will be seen below, one aspect of the present invention addresses this problem.

Site-specific soil sample analysis requires the collecting not only of soil analysis data, but also of locational data describing from where within the field each sample was obtained. While this can conceivably be done using traditional manual measuring, triangulating, or surveying methods for a few sample sites, it has been found more practical to use Global Positioning System (GPS) or Differential Global Positioning System (DGPS) techniques and devices, which are available and sufficiently accurate and repeatable. GPS and DGPS antennae, receivers, and signal conditioning I/O devices may be mounted to agricultural vehicles and interfaced to mobile control, computing, and datalogging devices.

Analysis is generally done later (off-line) in a laboratory. Sample site locational information may be marked on sample containers for later correlation with analysis data, or sample containers may be numbered or otherwise uniquely identified and those identifications tabulated with corresponding locational descriptions. In either case, the data correlation is a separate operation with an attendant cost.

Particularly in the harvesting of grain crops, grain flow rate into a harvesting machine's hopper and grain moisture content level are sometimes measured as an indication of crop yield. This measurement is most easily done in real time with transducers or measuring devices producing data signals representative of grain flow rates and moisture levels. These data may be logged into a data base in computer memory or otherwise recorded in real time, but the soil analysis data, obtained later off line, must be merged into the same database when they become available.

These data, as well as any other which may be desired and available, may be used to generate or update a precision farming prescriptive map. Prescriptive map data may be loaded in a portable memory device such as a diskette or PCMCIA card, which may then be used in a computer or PLC on board the vehicle to provide site-specific control setpoints to an on-board proportional control system which, with suitable signal conditioning and actuators, controls rate of farm input to the field in conformance with the prescriptive map.

The effect of repeatedly (e.g., annually) providing prescriptive varied farm inputs to a field is at least partially cumulative for some types of field spatial variation, providing a smoothing effect on field spatial variations after some repetitions of the precision farming cycle from tillage to harvest. The cumulative effect also makes it beneficial, however, to repeat the site-specific soil analysis at least annually in order to not oversupply field inputs to sites or areas which still show beneficial effects from previous spatially-varied input operations. The cost of a separately performed traversing of the field for soil sampling purposes alone would therefore be incurred annually. Accordingly, it would be desirable to provide a system for obtaining and locationally identifying site specific soil samples from an agricultural field while work is being performed in the field.

SUMMARY OF THE INVENTION

The present invention relates to an agricultural system for the acquiring of soil samples from a field of land. The system comprises a vehicle movable across the field and including an implement configured to perform at least one agricultural operation while in motion, a soil sample acquiring apparatus supported by the vehicle and configured to acquire samples of soil from the field while the vehicle is in motion, a location signal generating circuit supported by the vehicle, and means supported by the vehicle for recording the location within the field of the source of each sample.

In another embodiment of the invention, the system further comprises an apparatus supported by the vehicle for placing each sample into an individual container, which container may be connected to another individual container, and an apparatus supported by the vehicle configured to apply a unique identification upon each individual sample container. The unique identification may be an alphanumeric indicia which is incremented for each sample, and the system may further comprise a memory device supported by the vehicle and a control circuit supported by the vehicle and connected to the location signal generating circuit and to the memory, and configured to correlate each sample designation with the corresponding locational data to form a data set and to store the correlated data sets in the memory device. Sample designations may be applied to the corresponding containers as bar codes. The memory device may be portable and configured for uploading to a data base in a remote data processing apparatus for off line analysis of the soil samples.

In another embodiment of the invention, the system further comprises a memory device, an apparatus supported by the vehicle for analyzing the soil samples at the vehicle in real time, and a control circuit connected to the location signal generating circuit and the soil sample analyzing apparatus, configured to cause the analyzer to analyze the soil samples, correlate the analyses data with the corresponding locational data, and store the correlated data sets in the memory device. The memory device may be portable and configured to upload data off line to a data base located in a remote data processing apparatus. The memory device may be located remotely and may be in communication with the vehicle-supported control circuit through a wireless data link, the control circuit being configured to upload the correlated data sets to the remote memory device.

Another embodiment of the invention further comprises a plurality of vehicles which are equipped as above whereby they may upload data through a communication network in real time and substantially concurrently to the remote memory device. The vehicle-supported control circuit and the remote memory device may be configured for two-way communication, whereby the vehicle may upload data to the remote memory device in real time and the remote memory device may download prescriptive map data, and other data as desired, to the vehicle. The vehicles may exchange data through a communications network in real time and substantially concurrently with the remote memory device and with each other.

According to another aspect of the invention, a method is disclosed for acquiring a plurality of soil samples from an agricultural field of land while work is being performed on the field by a work vehicle moving over the field, the vehicle including an agricultural implement, the method comprising the steps of (a) acquiring samples of the soil utilizing a sample acquiring device, the device movably supported by the vehicle as means for the device being stationary with respect to the soil while the sample is acquired; (b) receiving location signals; (c) processing the location signals in a control circuit supported by the vehicle to generate location data representative of the plurality of locations; and (d) recording the location data.

According to another aspect of the invention, the method further comprises the steps of (e) placing each soil sample into an individual container, which containers may be connected to each other, and (f) uniquely identifying each container. The unique identification may be an alphanumeric indicia which is incremented for each sample and is applied to the corresponding container. The method may further comprise the steps of (g) correlating each unique identification with the corresponding locational data, and (h) storing the correlated data sets in a memory device supported by the vehicle. Each unique identification may be applied to the corresponding container as a bar code. The memory device may be portable and the method further comprise the steps of (i) transferring the correlated unique identification and locational data from the portable memory device into a data base in a remote data processing apparatus, and (j) scanning the unique identification indicia bar coded upon the container into the data processing apparatus to facilitate correlating of the corresponding off line sample analysis data.

According to another aspect of the invention the unique sample designation is the sample source location description, and the method further comprises the steps of (g) applying each unique sample identification to the corresponding container as a bar code, and (h) scanning each bar coded sample identification into a data base in a remote data processing apparatus.

According to another aspect of the invention, the method may alternatively additionally comprise the steps of (e') analyzing the soil samples at the vehicle to produce soil data in real time, (f') correlating each sample's soil data with the corresponding locational data to form data sets, and (g') storing the data sets in a portable memory device supported by the vehicle, and (h) uploading the portable memory device off line to a data base in a remote data processing apparatus.

According to another aspect of the invention, the method may alternatively additionally comprise the steps of (e") analyzing the soil samples at the vehicle to produce soil data in real time, (f") correlating each sample's soil data with the corresponding locational data to form data sets, and (g") uploading the data sets in real time via a wireless data link to a data base in a remote data processing apparatus, which data link may be additionally used to download prescriptive map data, and other information as desired, from the remote data processing apparatus to the control circuit at the vehicle.

According to another aspect of the invention, the method may additionally include the step of (h") communicating soil and locational data, and other information as desired, through a communications network by a plurality of vehicles with the remote data processing apparatus and with each other in real time and substantially concurrently.

In all embodiments of the invention described above, the data base may be a geographic information system (GIS) program and the location signal generating circuit may be a global positioning system (GPS) which may be provided with an associated differential global positioning system (DGPS).

BRIEF DESCRIPTION OF THE DRAWINGS

The invention will become more fully understood from the following detailed description, taken in conjunction with the accompanying drawings, wherein like reference numerals refer to like parts.

DETAILED DESCRIPTION OF THE PREFERRED EMBODIMENTS

Figure 1:
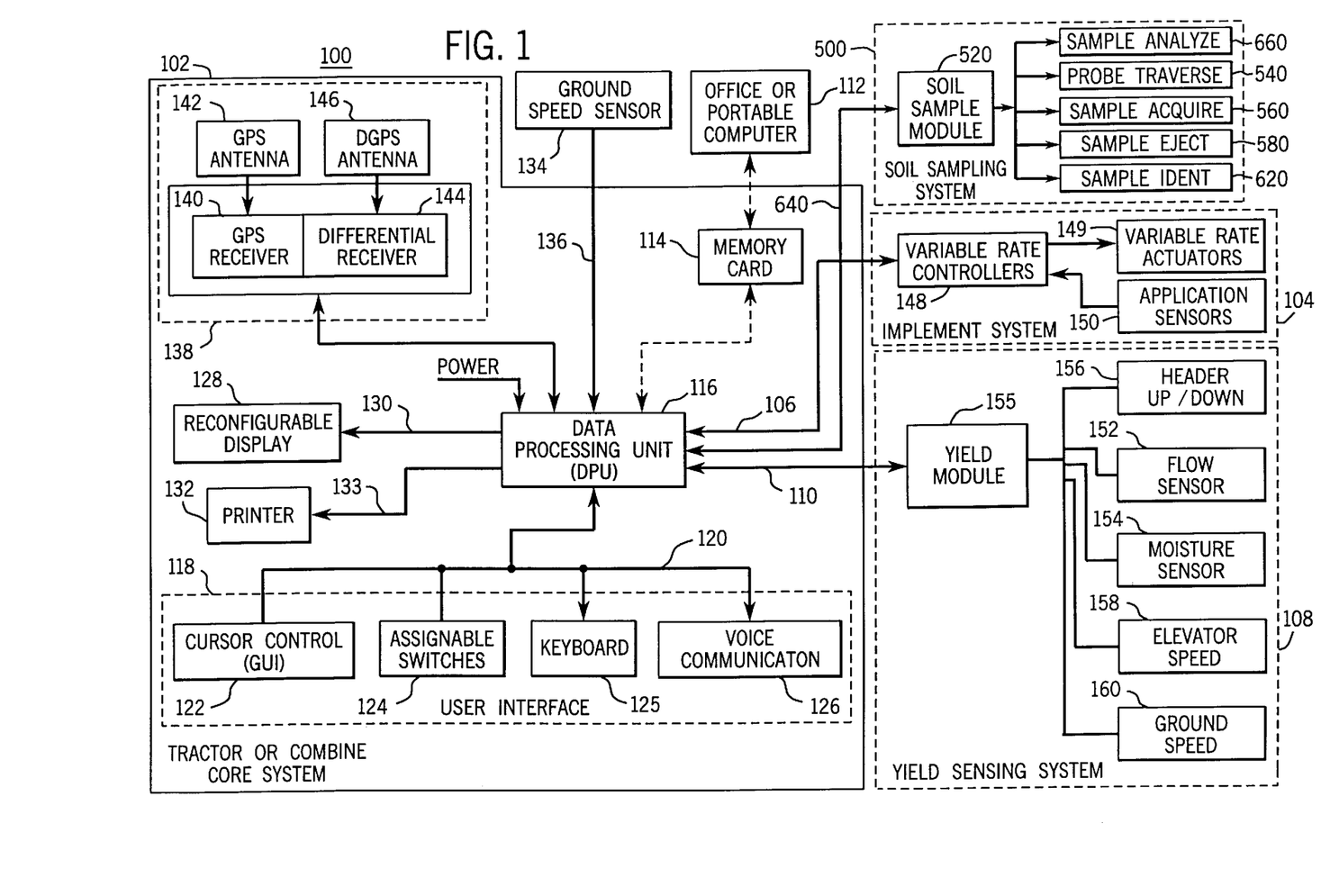
FIG. 1 is a block diagram illustrating a site-specific farming system including a vehicle equipped with a soil sampling system, sensors for sampling site-specific characteristics of a field and a crop growing thereon, and electronic displays for displaying visible indicia of the characteristics in the vehicle cab, in an office, or at a portable computer.

Referring to FIG. 1, a site-specific farming system 100 includes one or more core systems 102, supported by one or more agricultural vehicles such as tractors or harvesters. The core systems 102 provide data processing functions for the agricultural vehicles, and each vehicle is equipped with its own core system 102. Each vehicle also includes an implement system 104 appropriate for the task at hand (e.g., tilling, planting, spreading, harvesting, etc.) and with a soil sampling system 500. Core system 102 communicates with implement system 104 over a bus 106 and with soil sampling system 500 over another bus 640. If the agricultural vehicle being used is a harvester, it may be equipped with a yield sensing system 108 that communicates with core system 102 over a bus 110.

Preferably, core system 102 is removable and can be installed on a variety of agricultural vehicles including an implement system 104. Core system 102 can be configured to operate in an APPLY mode wherein it collects, controls, records and displays specific monitored data while an implement function is active (e.g., tilling, planting, spreading, etc.). Alternatively, core system 102 can be configured to operate in a general DATA COLLECTION mode wherein it collects, controls, records and displays all monitored data. The displayed data may include previously recorded data or the actual monitored data of the parameters presently being controlled.

When installed on a vehicle equipped with a soil sampling system 500, core system 102 can be configured to operate in an APPLY or DATA COLLECTION mode wherein it collects, records and displays application data; e.g., soil sample site locational data. The APPLY or DATA COLLECTION modes also correspond with the vehicle implement applying field inputs such as plowing. Core system 102 also provides directional or locational assistance during application of field inputs.

Farming system 100 also includes a workstation or personal computer 112 which may be located in the farm office or may be portable. A wireless medium of communication may be used to transfer site-specific data between core system 102 and computer 112. Core system 102 and computer 112 each may include a read/write interface (not shown) for a removable memory device 114 which can be transported between core system 102 and computer 112. Memory device 114 is used to transfer site-specific data from core system 102 to computer 112, and to transfer prescriptive maps from computer 112 to core system 102. Memory devices 114 may be Type II PCMCIA cards made by Centennial Technologies, Inc. However, other mediums of data storage (e.g., floppy or portable hard disk, EPROM module, etc.) may be used.

Core system 102 includes a digital data processing unit (DPU) 116 which communicates with the vehicle operator through a user interface 118 via a link or links 120 (e.g., an RS-232/485 interface; a standard keyboard interface). DPU 116 is a PC CPU and includes a microprocessor, system clock, non-volatile memory (e.g., PROM, EPROM or FLASH), volatile memory (RAM), and a power supply. The microprocessor executes a program stored in non-volatile memory. The volatile memory (RAM) may be provided with a battery back-up circuit. Alternatively, DPU 116 may be implemented using dedicated, specific purpose equipment or hard-wired logic circuitry. User interface 118 may include a graphical user interface (GUI) 122 providing cursor control (e.g., a mouse, trackball, joystick, or fourway switch with up, down, right and left positions), assignable switches 124 (e.g., push buttons) configurable by the processor, a keyboard 125, and/or a voice-communication interface 126.

DPU 116 is configured to generate display signals which are applied to a reconfigurable display 128 (e.g., a CRT or flat screen LCD display) via a communication link 130. Display 128 is preferably an active matrix LCD capable of displaying full-motion video and a number of colors under widely varying ambient light conditions. Display 128 is also capable of displaying graphics and alphanumeric characters. Display 128 is used, inter alia, to display the current configurations of assignable switches 124. DPU 116, user interface 118 and display 128 may be located in the vehicle cab such that the operator has easy access to user interface 118 and an unobstructed or substantially unobstructed view of display 128. Core system 102 may also include a printer 132, or a plotter or similar device, in the cab which communicates with DPU 116 via an interface 133 (e.g., an RS-232 link). A printout of soil, locational, and other data may be scanned into the remote computer 112 for entry of data into a data base, if desired, instead of using the portable memory device 114.

DPU 116 may receive signals representing the speed of the vehicle from a ground speed sensor 134 via an interface 136 (e.g., a frequency interface). Ground speed sensor 134 may include a magnetic pickup sensor configured to sense the speed of the vehicle's wheels or transmission, or may include a radar device mounted to the body of the vehicle. The latter is preferred to preclude measurements made false by, for example, slippage of drive wheels in wet or loose soil. The speed signals may be integrated by DPU 116 to compute distance travelled.

DPU 116 also communicates with a location signal generation circuit 138 which generates location signals representing the vehicle's location. Circuit 138 includes a global positioning system (GPS) signal receiver 140 with an associated antenna 142, and a differential GPS (DGPS) signal receiver 144 with an associated antenna 146. A single antenna may be used in place of antennas 142 and 146. GPS receiver 140 may, for example, be manufactured by Trimble Navigation Ltd. of California, and DGPS receiver 144 may be manufactured by Satloc, Inc. of Arizona. GPS receiver 140 determines longitude and latitude coordinates (and altitude) of the vehicle from signals transmitted by the GPS satellite network. The accuracy and repeatability of the location data are improved by applying correction signals received by DGPS receiver 144. The differential correction signals are used to correct errors present on GPS signals including the selective availability error signal added to GPS signals by the U.S. government. DGPS signals are transmitted by the U.S. Coast Guard and by commercial services. For example, the Omnistar DGPS system from John E. Chance & Assoc. of Texas includes a network of ten land-based differential reference stations that send correction signals to a master station which uploads signals to a satellite for broadcast throughout North America. GPS differential correction signals may also be transmitted from a local base station. In a preferred embodiment, DPU 116 interfaces with SATLOC L-Band Integrated Terra Star DGPS System via an RS-485 communication link.

When core system 102 is mounted on a vehicle, DPU 116 communicates with soil sampling system 500 via a bus 640 and with implement system 104 via another bus 106. Communication of soil sampling system with DPU 116 is generally similar to communication of implement system 104 with DPU 116, which has been discussed above.

Implement system 104 may include one or more variable-rate controllers 148, variable-rate actuators 149, and application sensors 150. DPU 116 reads application rate data for a particular field location from a prescriptive map (which may be supplied by computer 112), or reads an input device such as a potentiometer (not shown) used to manually set a desired application rate, and generates commands which are sent to variable-rate controllers 148. The command output rate is a function of the speed of the vehicle and the desired application rate. For example, an increased speed will require an increased output rate to maintain a constant desired per-foot application rate. In response, controllers 148 generate control signals which are applied to variable-rate actuators 149. Application sensors 150 may provide feedback signals representing the actual application rates to enable closed-loop control. Bus 106 may be an RS-485 bus for a single-channel variable-rate controller, or an SAE J-1939 implement bus for a multiple-channel controller.

Core system 102 may communicate with other vehicle systems over a vehicle data bus (not shown). Preferably, the vehicle data bus conforms to the standards of SAE J-1939 ("Recommended Practice for a Serial Control and Communications Vehicle Network"). A bridge circuit may be used to facilitate the transfer of data between the vehicle data bus and a secondary implement bus coupled to implement system 104 and DPU 116. The bridge circuit may be used to filter data between busses, thereby decreasing bus loading.

Figure 2:
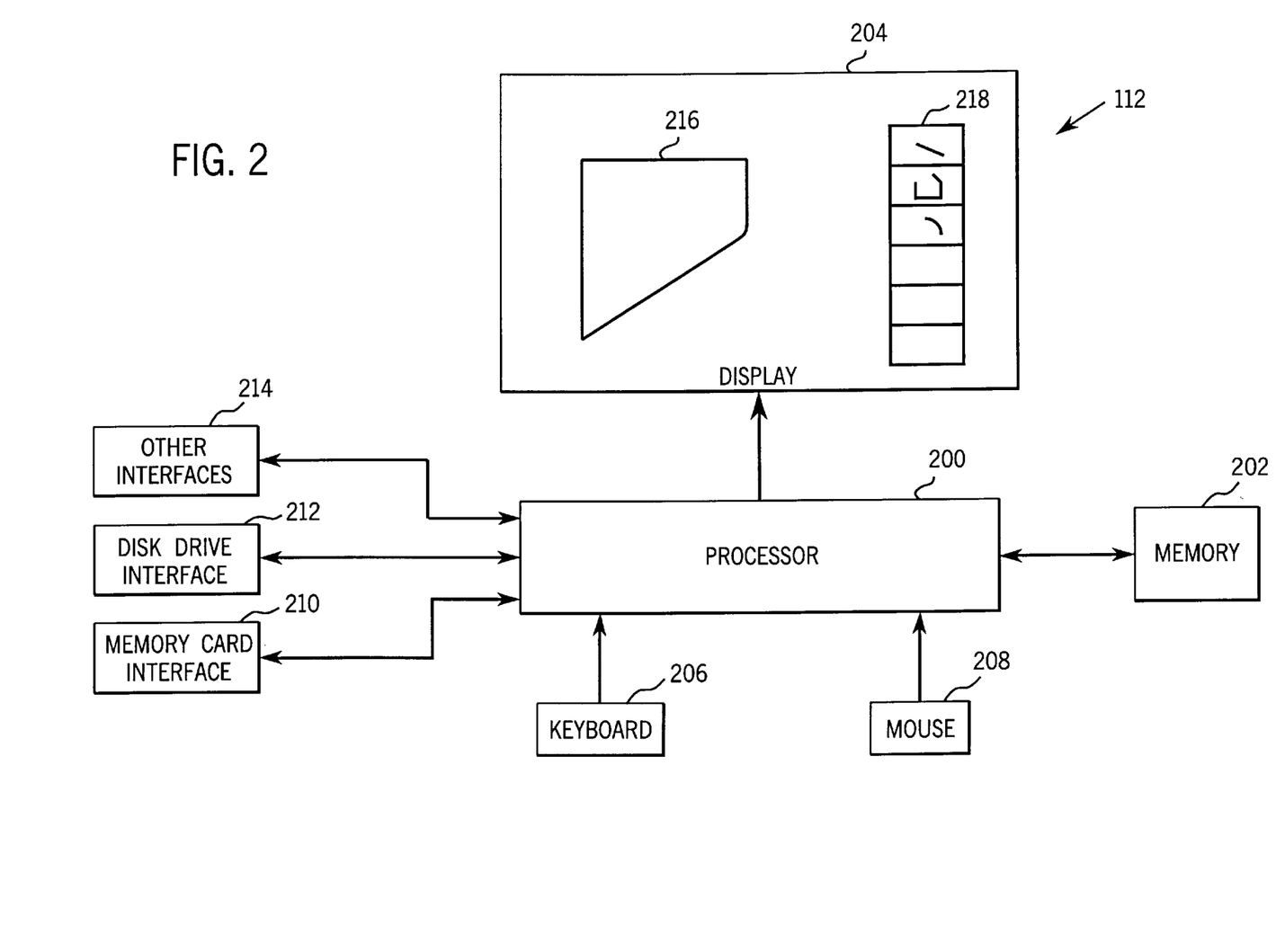
FIG. 2 is a block diagram of the office or portable computer shown in FIG. 1 which can be used to process site-specific soil sample, and other farming, data.

Referring to FIG. 2, computer 112 is preferably a programmed personal computer including a processor 200, a memory circuit 202, a color or monochrome display 204, input devices such as a keyboard 206, and/or a mouse 208, and input/output interfaces such as a memory device interface 210, a hard or floppy disk drive interface 212, and other interfaces 214 (e.g., RF or infrared). An input device such as a joystick, light pen, or touch screen may also be used. Alternatively, computer 112 may be implemented using dedicated specific-purpose equipment or hard-wired logic circuitry. Processor 200 may include a microprocessor configured to execute a program stored in memory 202 or on a disk read by disk drive interface 212. Processor 200 may read precision farming data including position information from memory device 114 using memory device interface 210. Data may also be entered using keyboard 206, mouse 208, disk drive interface 212, or another interface 214 such as a scanner of hardcopy printout generated on the vehicle during field operations.

Processor 200 generates display signals which, when applied to display 204, cause visual alphanumeric and graphical indicia to be displayed. For example, the display signals may cause display 204 to create a visual map 216 of a field as well as icons 218 representing drawing tools in a toolbox. Preferably, display 204 is a color monitor, but it may instead be a monochrome monitor capable of displaying different light intensity levels.

Figure 3:
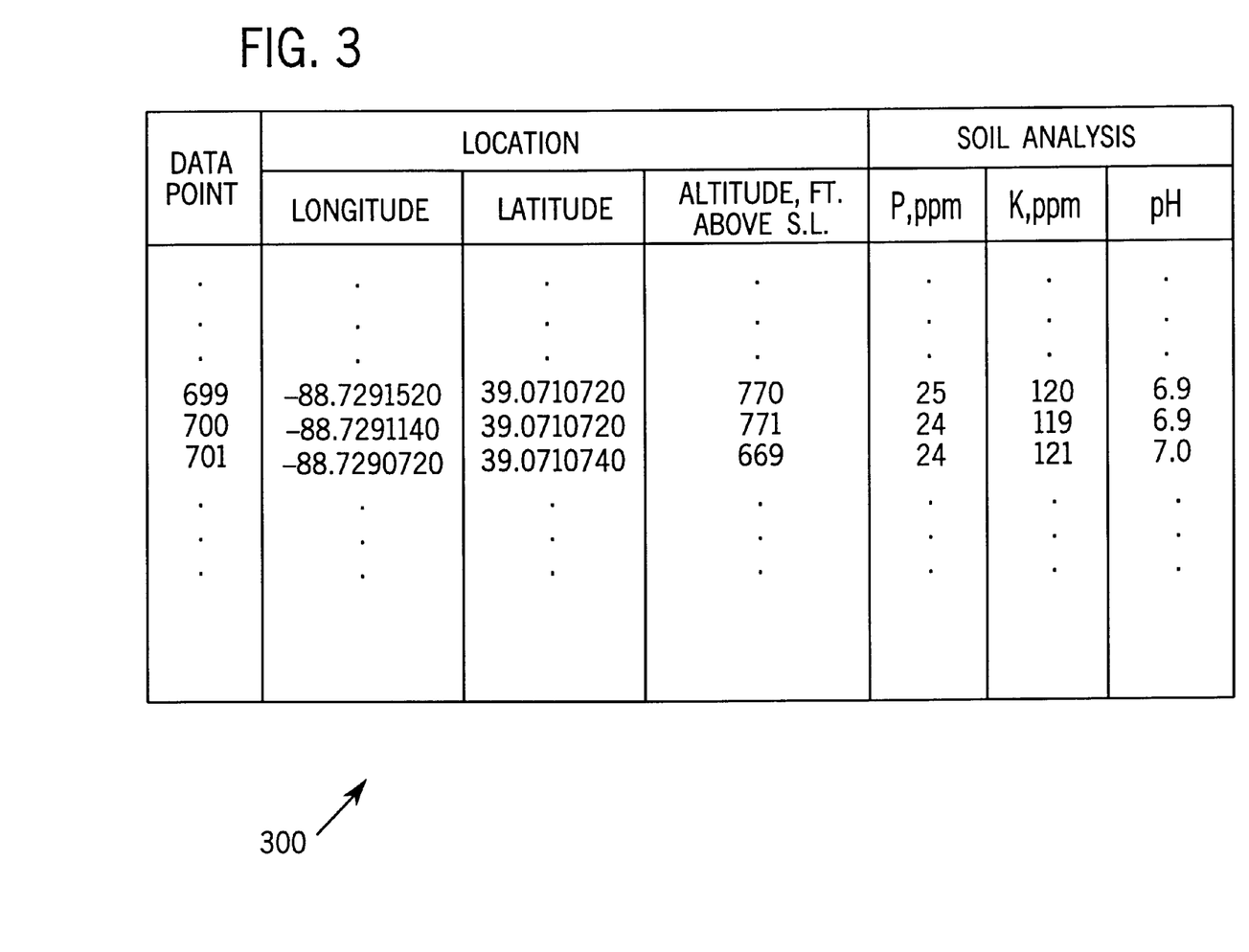
FIG. 3 represents a layer of spatially-variable data stored in memory and showing the analysis of several soil samples and their source locations within the field.

FIG. 3 generally represents the structure in which a layer of site-specific soil data representative of soil analyses in a farming field is stored in memory. The data structure may be referred to as a layer in a geo-referenced digital map. The structure is preferably implemented using a database 300 (e.g., a geographical information system (GIS) database) represented by a table, wherein each row represents a data point taken at a location in the field. For example, a layer having 5000 data points is represented by a table having 5000 rows. Columns of information are associated with each data point. For example, the columns shown in FIG. 3 include soil constituent and acidity data, and the longitude and latitude coordinates and altitude at which each data point was sampled.

A similar structure may be used to store each layer of site-specific farming data. For example a soil pH layer may include a row for each data point and columns for pH, longitude, latitude, and altitude. Thus, memory device 114 may contain a layer of data for each site-specific characteristic of a field. The data structure may also include heading information such as a vehicle identifier, a farm identifier, a field identifier, and a serial number for hardware components of farming system 100 (e.g., a yield module serial number). A similar data structure may be used to store harvest data as well as application data. The harvest and application data are also stored in memory device 114.

DPU 116 and processor 200 use soil, and other, data and correlated location data to perform various functions of site-specific farming system 100. For example, DPU 116 or processor 200 use the correlated farming data to generate display signals which cause electronic display 128 or 204, respectively, to plot a map of a field which includes visible indicia of the soil constituents. DPU 116 typically plots the map in real time as the analysis and location signals are received from the measuring and analyzing devices and from location signal generation circuit 138, respectively. However, DPU 116 may also plot a map off-line based upon farming data previously stored in memory. For example, if an application operation was stopped in mid-field on a previous day, DPU 116 may generate a map based on the previous day's data and continue plotting on the data map that is collected during the current day's operation. In contrast, processor 200 typically plots the map off-line based upon farming data received from the memory device 114.

Figure 4:
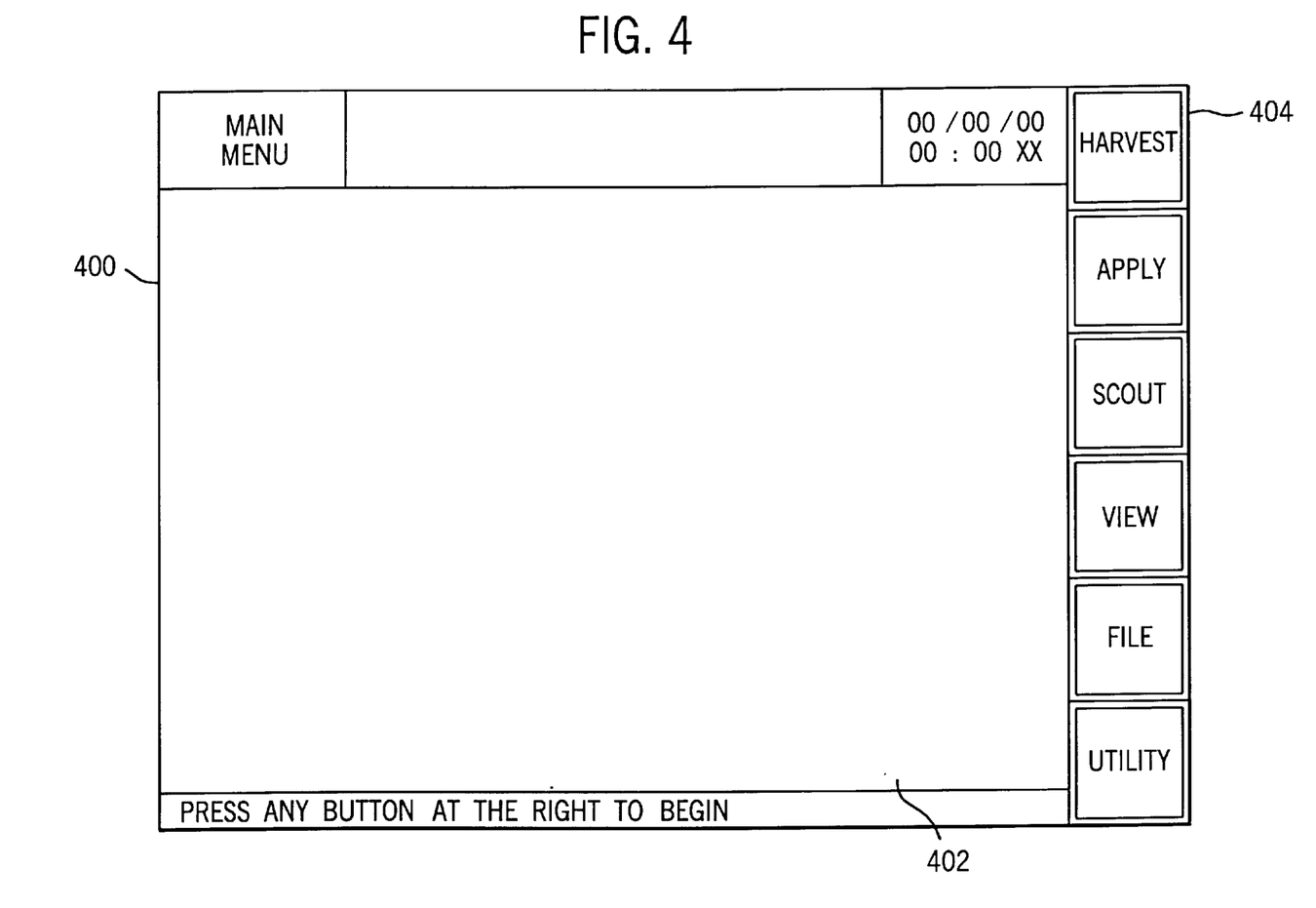
FIG. 4 shows a main menu screen on the electronic display in a vehicle cab shown in FIG. 1 when power is applied to the site-specific farming system.

Site-specific farming system 100 operates in one of several modes selected by the operator. Referring to FIG. 4, DPU 116 generates display signals after power is applied to farming system 100 which cause display 128 to display a main menu screen 400 in the vehicle cab. The screen 400 of display 128 includes a map display area 402 which displays an introductory message (not shown) and a graphical operator interface 404 which shows the initial configuration of assignable switches 124. On powerup, the switches are assigned functions which correspond to the operating modes of DPU 116 including HARVEST, APPLY, SCOUT, and, alternatively, DATA COLLECTION (not shown). DPU 116 reads signals generated in response to operator actuation of one of the switches 124, decodes the signals, and enters the selected mode of operation.

Figure 5:
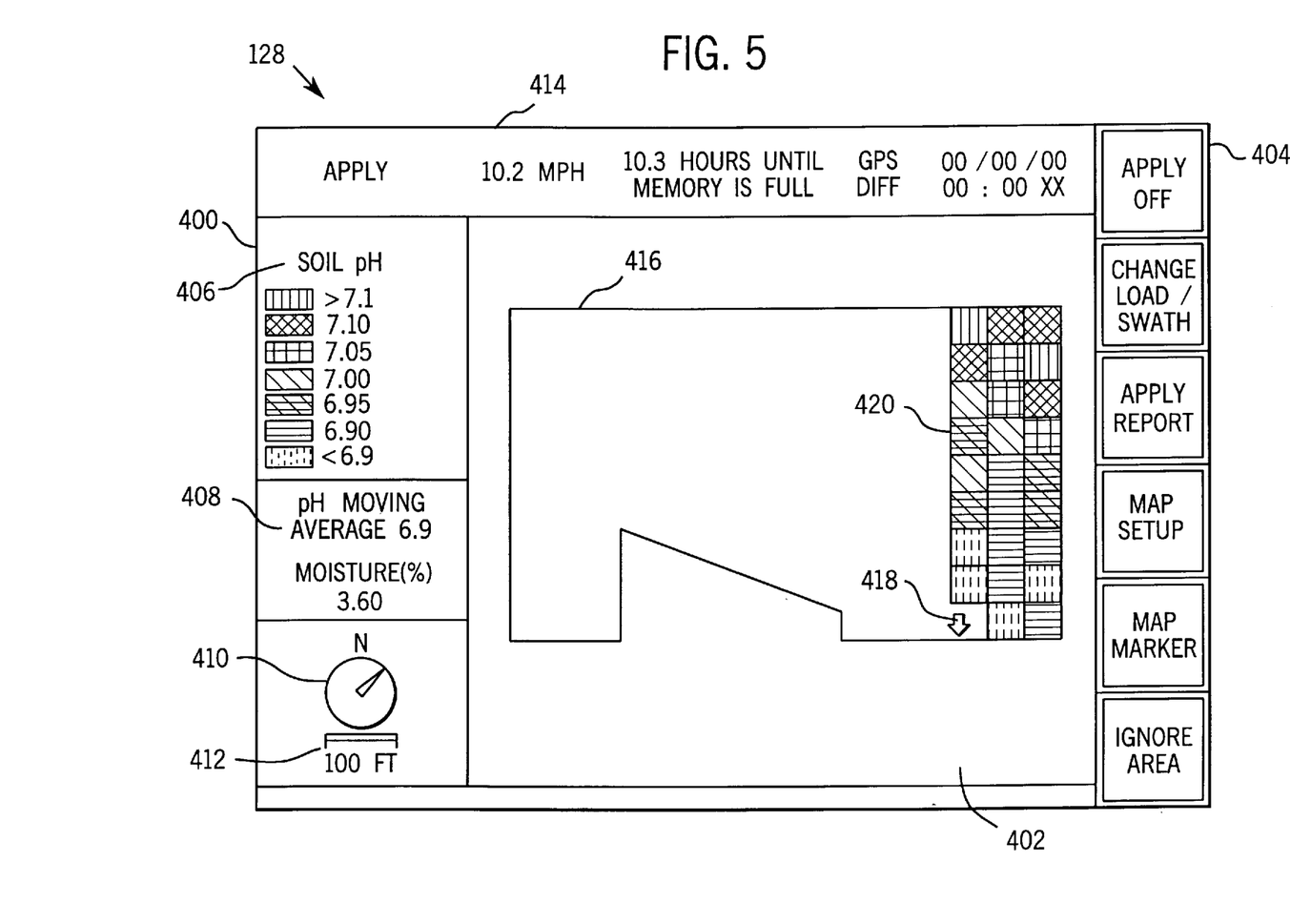
FIG. 5 shows an application screen on an electronic display in a vehicle cab which indicates a map of a field, visible indicia of soil analyses, and visible indicia showing the definitions of a plurality of redefinable switches when configured for applying field inputs.

When farming system 100 is in position to provide farming inputs to a field, the switch 124 corresponding to APPLY in FIG. 4 is actuated. In response, DPU 116 enters into APPLY mode and generates display signals which cause display 128 to show an APPLY screen as depicted in FIG. 5. As application of farming inputs begins, soil data and correlated location data are gathered and used to generate display signals causing display 128 to plot a map of the field in map display area 402 including visible indicia of soil analysis if analysis is being done in real time, depth of soil engagement of a tillage device such as a plow if being measured, or whichever other parameters may be of interest. DPU 116 also changes the configuration of switches 124, and generates display signals causing operator interface 404 to generate visible indicia showing the new states or configurations of switches 124. As shown in FIG. 5, assignable switches 124 have been redefined to generate input signals which relate to applying field inputs (e.g., "APPLY OFF", "CHANGE LOAD/SWATH", "APPLY REPORT").

The display signals also cause display 128 to show a legend block 406, a status block 408 for displaying statistical data of the field, a compass indicator 410 to show the heading of the vehicle, a map scale 412, and a status line 414 for displaying status information such as the operating mode (HARVEST, APPLY, DATA COLLECTION, or SCOUT), the vehicle speed, time remaining until memory device 114 is full, GPS and DGPS status (e.g., "good" or "bad") and date/time. The graphical symbols and their positions within screen 400 are shown for illustration only and may be modified. For example, map display area 402 may cover any portion of or all of screen 400 with other displayed information superimposed or suppressed if necessary.

FIG. 5 represents an exemplary display when core system 102 is mounted on a vehicle equipped with soil sampling system 500 and other application sensors 150, including a moisture sensor, and the vehicle is applying field inputs. In this example, the boundaries of the field being worked are defined and are stored in memory. After entering the APPLY mode of operation, in response to actuation of one of assignable switches 124, DPU 116 accesses the longitude and latitude coordinates of the field boundary from memory and scales the field boundary to substantially correspond to a portion of map display area 402. DPU 116 scales the boundary data and produces display signals which, when applied to display 128, generate a visible map 416 of the field within the portion of the map display area 402. The portion of map display area 402 which is used to display map 416 may be 80% or 90% of the size of map display area 402, with the percentage selected to enhance the visual appearance of map 416. However, any percentage value may be used which provides a desirable appearance, including 100%, and the value may be set by the user. The scale of map 416 is displayed at indicia 412 (e.g. 100 ft/inch).

At the start of the field operation process, the vehicle was located at the upper-right hand corner of map 416. The vehicle then made a number of passes through the field, turning at the headlands (located at the boundaries of map 416). The current location of the vehicle is marked by an icon 418, such as an arrow which also indicates the direction of travel which may be determined from changes in the location data. Other icons may be used (e.g., a schematic or outline drawing of a vehicle). Throughout the field operation process, DPU 116 gathers site-specific data sensed by soil sampling system 500 and other application sensors 150 and correlates the sensed data with the locations at which the sensed data was sampled using signals from location signal generation circuit 138. The correlated data is stored in memory (e.g., memory device 114) for later analysis by office computer 112.

DPU 116 provides an indication of the time remaining before memory device 114 is filled up by soil and application data during APPLY mode, or by soil and yield data during HARVEST mode when core system 102 is on a harvester. The time remaining equals the amount of memory currently free multiplied by the time since the start of application or harvesting, divided by the difference between the amount of memory free at the start and the amount of memory currently free. The result of the calculation is displayed in status line 414 (e.g., "10.3 Hours Until Memory is Full"). Alternatively, DPU 116 may display the portion or percentage of memory device 114 that is filled up.

DPU 116 may also provide an indication of the estimated time remaining until sampling of the field is complete (i.e., estimated time to complete application or harvesting). The estimated time to complete equals the time since the start of application or harvesting multiplied by the difference between the area of map 416 within the boundaries and the area worked, divided by the area worked. The result is displayed on display 128 (e.g., "Estimated Time to Complete is 3.5 Hours"). Alternatively, DPU 116 may display the portion or percentage of the field that has been harvested.

To accurately correlate locational data with soil data, DPU 116 is preferably programmed with variables, which may be set by the operator, which indicate the distance and direction between GPS antenna 142 and the sample site location (i.e., between antenna 142 and the sample acquiring apparatus. This information is used as an offset to correct the location data stored with the sensed data. In one embodiment, DPU 116 maintains a buffer of the last 20 locations received, and selects a location to use based upon the delay value. The soil data and correlated location data are used to produce a display signal in real-time which, when applied to display 128, generates visible indicia of the soil constituents at corresponding locations of map 416.

DPU 116 may gather data over rectangular, or substantially square, areas of the field where the sides of the square may be substantially equal to the width of cut of the harvester or operating width of the implement. Other grids or blocks may be used. Data within each block may be automatically filtered (e.g., averaged). Filtering data eliminates the need to plot every data point, thereby decreasing bus loading and visual noise on display 128. If desired, the blocks of filtered data rather than the raw data could be stored in memory to reduce the memory storage and subsequent processing requirements. The filtered value of the data in each block, and location data associated with the block (appropriately scaled), are used to produce the display signal applied to display 128. In response, display 128 generates visible blocks 420 which include visible indicia of the filtered soil analyses at corresponding locations of map 416.

Data may be visually represented on display 128 in several ways. In a preferred embodiment, distinguishable colors represent different ranges of the average data in each visible block. For example, the colors red, orange, yellow, green, cyan, blue and violet may represent increasing ranges of value of a parameter being measured; legend 406 displays each color and its associated value range. The ranges and colors are not limited to this configuration. Further, the range and color schemes can be either automatically selected or can be manually selectable by the user. Alternatively, ranges may be represented by alphanumeric characters or by different light intensity levels or by shades of grey.

Graphical operator interface 404 includes a label which shows the assignment currently selected for each switch 124. The label and assignment depend on the mode of operation of DPU 116. Indicator 410 is an electronic compass which shows the current direction or heading of the vehicle with respect to north (e.g., northeast in FIG. 5). DPU 116 may calculate the heading based on a vector from the previous location of the vehicle to the current location. Appropriate filtering may be used to stabilize the compass against dither when the vehicle is not moving. Alternatively, the vehicle may be equipped with a compass or gyroscope electronically interfaced with DPU 116. In FIG. 5, the orientation of the display shows the vehicle going up and down as it travels northeast. However, the orientation of the display could also be geographic (e.g., "north up").

In FIG. 5, status line 414 displays "APPLY" to indicate that DPU 116 is operating in APPLY mode, and operator interface 404 indicates that assignable or redefinable switches 124 are configured to generate input signals relating to application (e.g., "APPLY OFF", "CHANGE LOAD/SWATH", "APPLY REPORT"). However, when core system 102 is mounted on a harvester and is operating in HARVEST mode, status line 414 shows "HARVEST" and operator interface 404 indicates that re-definable switches 124 are configured to generate input signals relating to harvesting (e.g., "HARVEST OFF", "CHANGE LOAD/SWATH", "HARVEST REPORT").

Preferably, DPU 116, display 128 and switches 124 are packaged in an integrated bezel assembly such that display 128 provides labels showing assignments of adjacent switches 124. However, switches 124 could be housed in a keypad external to housing assembly of DPU 116, or could be configured in other ways, such as a single rotary selector switch.

Figure 6:
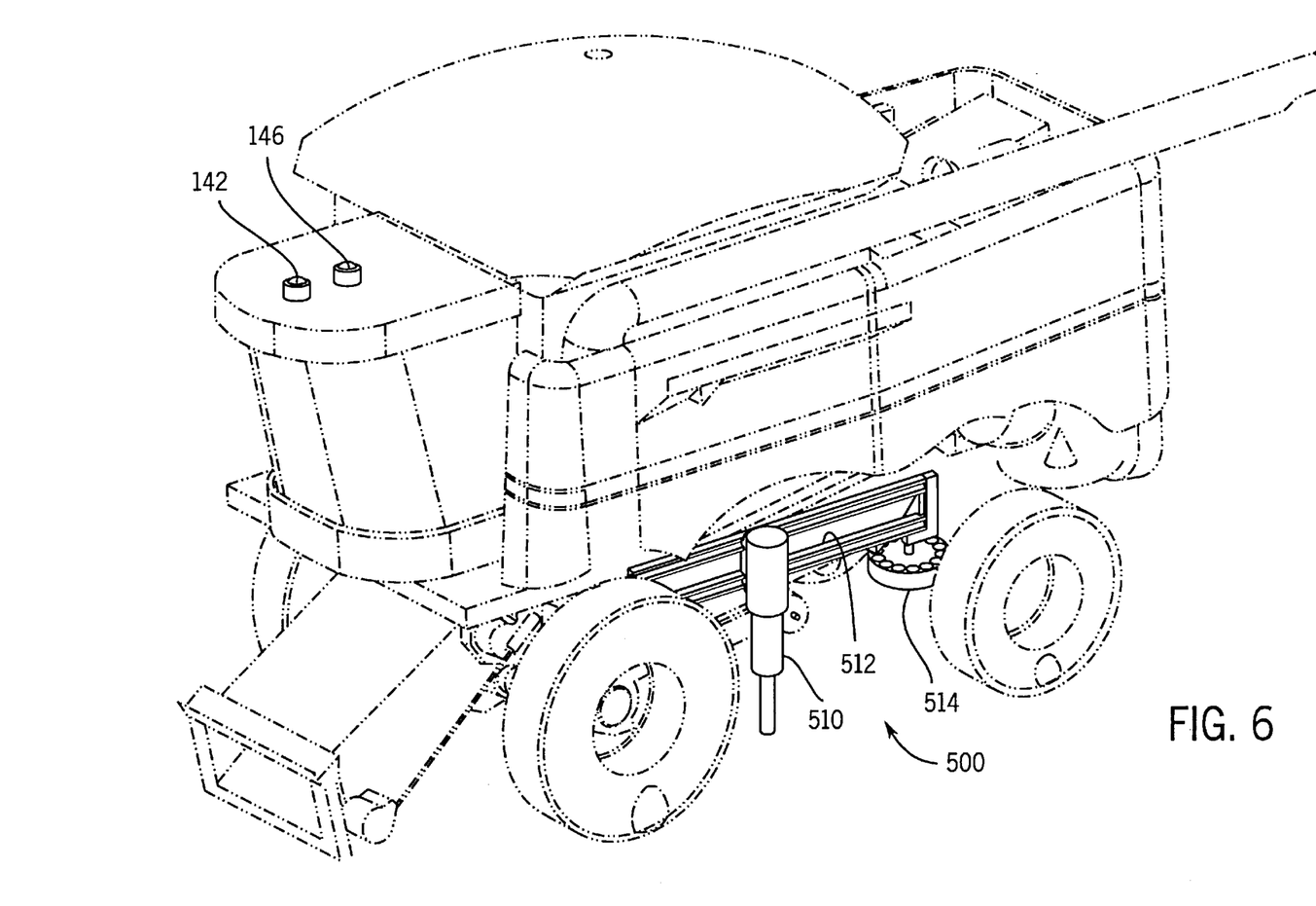
FIG. 6 is a perspective view of an embodiment of a movable soil sample acquisition device mounted upon an agricultural vehicle.

FIG. 6 shows a soil sampling system 500 configured for off-line sample analysis and including a soil sample acquisition device 510 movably mounted upon and coupled to a track assembly 512, track assembly 512 being mounted to an agricultural vehicle, in the illustrated instance to the side of a harvester. Soil sampling system 500 also includes an apparatus for the collecting and identification of samples, in the illustrated instance a carousel turntable 514 having a labelling device (not shown; e.g., an ink-jet printer).

Figure 7:
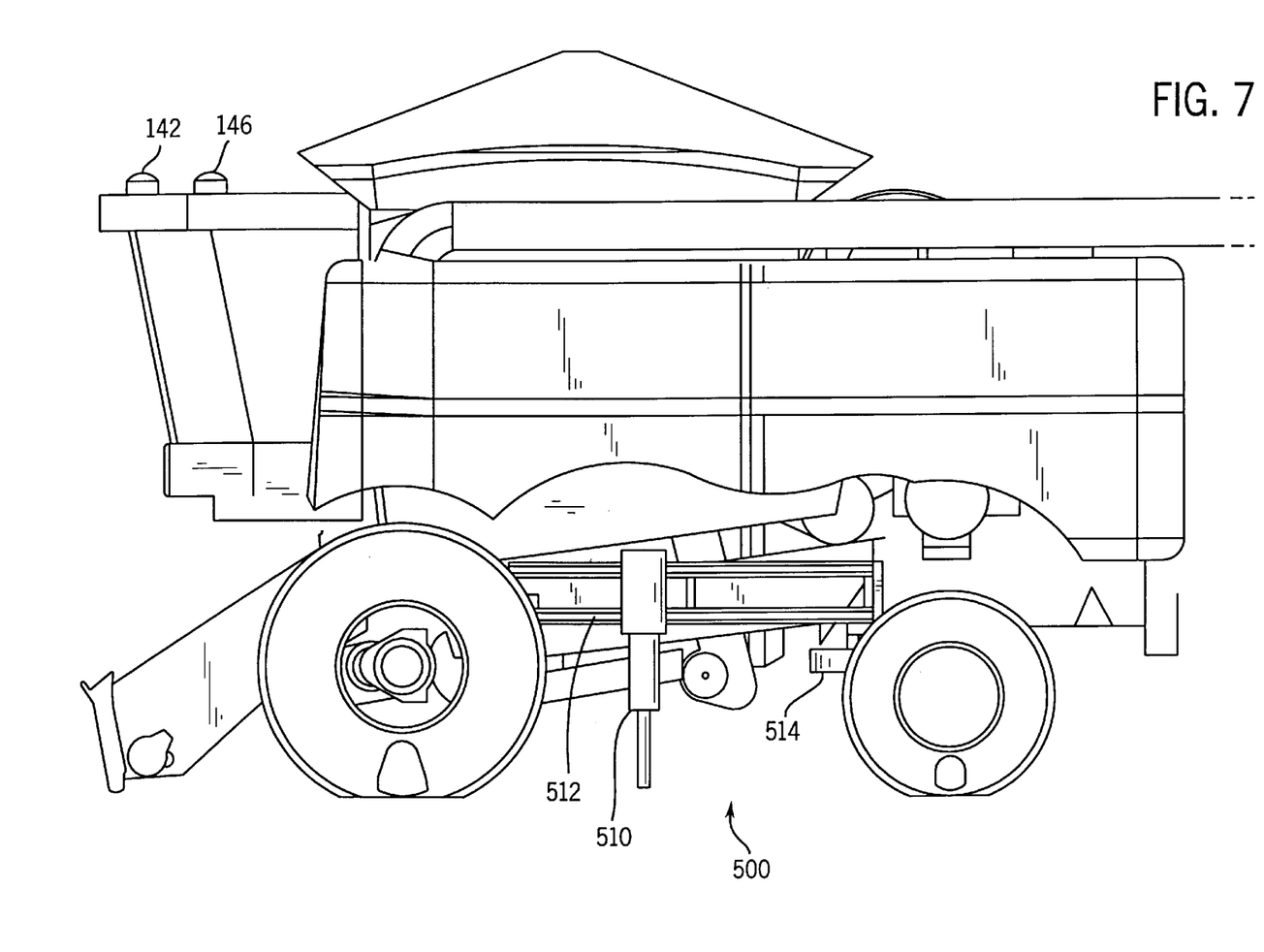
FIG. 7 is a side elevation view of an embodiment of a movable soil sample acquisition device mounted upon an agricultural vehicle.

The soil sampling apparatus shown in perspective relationship in FIG. 6 is shown in cutaway side elevation in FIG. 7 for clarification.

Figure 8:
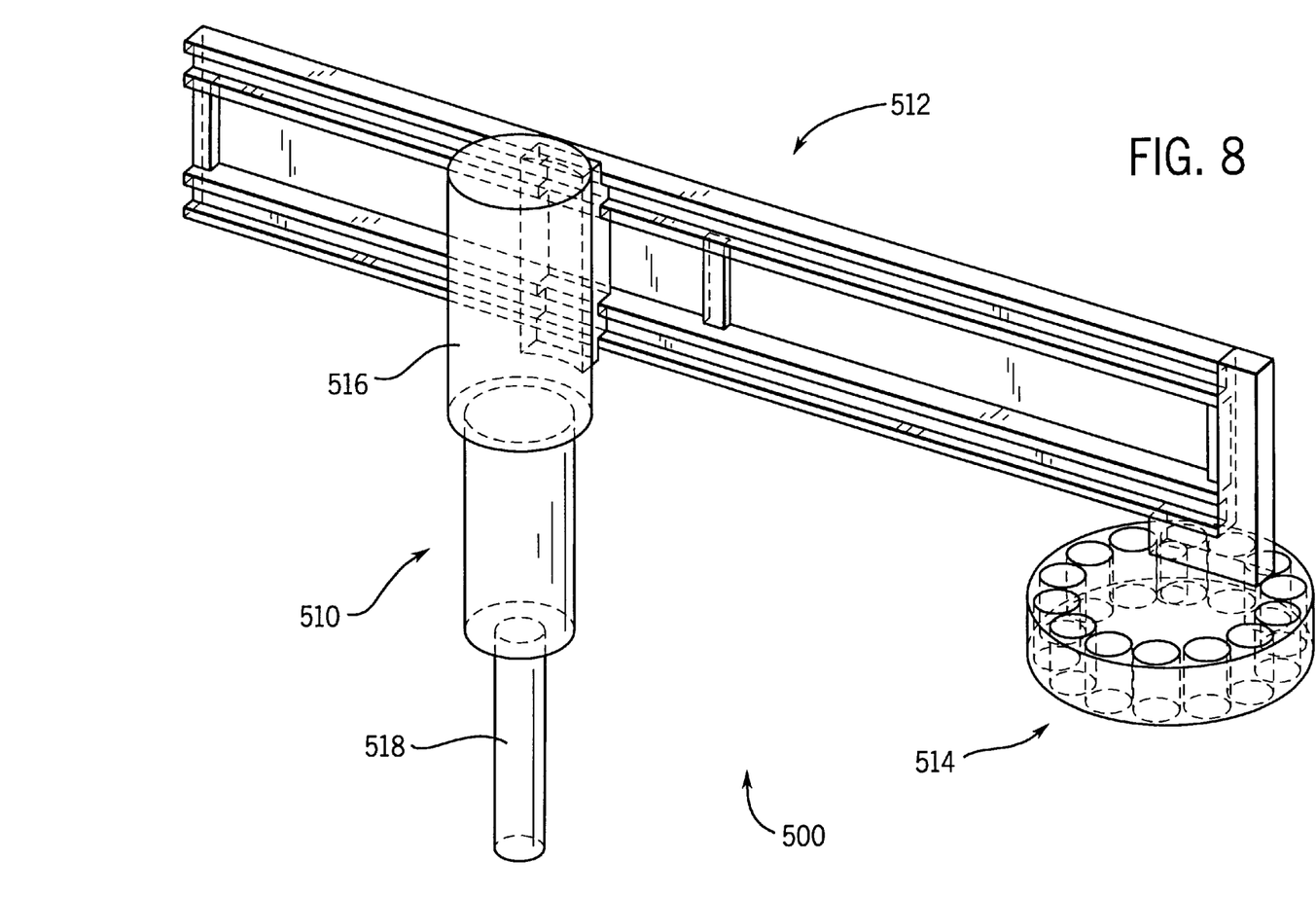
FIG. 8 is a perspective view of a movable soil acquisition device.

FIG. 8 shows soil acquisition device 510, track assembly 512, and sample collection device 514. Soil sample acquisition device 510 includes an actuating portion 516 and a soil engagement portion 518. Actuating portion 516 comprises in the preferred embodiment a hydraulic cylinder, but may alternatively comprise a pneumatic cylinder or an electro-mechanical linear actuator (e.g., an electric or hydraulic motor coupled to a leadscrew or ballscrew). Actuating portion 516 is configured to thrust soil engagement portion 518 into the soil to a predetermined depth, whereby soil engagement portion 518 may remove and retain a soil sample in the form of a plug of soil from the field.

Track assembly 512 is typically and approximately 3.5 meters long and is mounted upon the vehicle such that its major axis is disposed parallel to the direction of forward motion of the vehicle. Actuator portion 516 of soil sample acquisition device 510 is movably coupled to track assembly 512 so that it may move rearwardly with respect to the vehicle while soil engaging portion 518 of soil sample acquisition device 510 is engaged with the soil, whereby it may remain stationary with respect to the soil while engaged with the soil. In the preferred embodiment, track assembly 512 includes two spaced-apart steel channel tracks and upper actuating portion 516 includes sealed, polymer-tired cam follower bearings (not shown) retained upon the tracks by track flanges (not shown). Other embodiments will be obvious to those skilled in the art, such as tracks comprising rails of steel round stock or steel angles, cam followers provided respectively with radiused or vee-grooved peripheries, or slides comprising bushings or shoes constructed of bearing polymers. In any case, it is preferred for the at least one bearing devices engaging one of either the upper track or the lower track to be rigidly mounted to the actuating portion 516 and for the at least one bearing device engaging the other of the upper track or the lower track to be resiliently mounted to the actuating portion 516, whereby (a) at least a small amount of deformation of track assembly 512 may be tolerated and (b) at least a small amount of movement of soil engaging portion 518 with respect to the soil may be tolerated.

Soil sampling system 500, when configured for off-line analysis of samples, includes a track actuator (not shown) which traverses soil sample acquisition device 510 along the length of rail assembly 512. In the preferred embodiment, the track actuator is a hydraulic rotating motor provided with a toothed belt sheave and secured the rear surface of track assembly 512. A pulley (not shown) is provided at each end of track assembly 512, and a length of toothed belt stock is passed over the sheave and both pulleys and secured at each to the actuating portion 516, whereby rotation of the motor shaft will traverse soil sample acquisition device 510 over the length of track assembly 512.

When soil engaging portion 518 of soil sample acquisition device 510 has been plunged into the soil and begins to retract with a plug or sample of soil, a cover closes the open end of a hollow cylinder at the bottom of soil acquisition device 510 to retain the soil sample within the cylinder. The sample must then be stored and identified. This is performed by sample collection device 514, which is preferably located near the rear end of track assembly 512. Simultaneous retraction of soil engaging portion 518 with respect to actuating portion 516 and detection (e.g., by interruption of an infrared light beam within a chamber of soil engaging portion 518) of presence of soil within soil engaging portion 518 causes probe traverse module 540 to signal the track actuator to traverse soil sample acquisition device 510 to its rearmost position, where it engages sample collection device 514. Sample eject module 580 is then signaled by a limit switch (not shown) to cause a sample actuator (not shown) to transfer the sample to sample collection device 514.

Soil collection device 514 is provided with sample containers (not shown; e.g., plastic bags or cups) and with a sample container labelling device 620 (e.g., an inkjet printer or an applicator of self-adhesive labels which have been pre-printed in correspondence with the prescription map governing the sample acquisition locations within the field). While soil collection device 514 is shown in FIGS. 6 and 8 as a 14-station, single-tray carousel for simplicity, a carousel having multiple trays with automatic indexing of trays and at least 50 stations per tray is preferred to minimize the number of stops in the field operation being simultaneously performed for removal of filled sample containers and replacement by empty sample containers. The number of sample sites, "N", within a 100 acre field using a 30-foot sample site grid pitch is, for example:

$$N=\{[(43{,}560*100)^{1/2}]/30\}^2+1=4841$$

Speed of traversing of soil sample acquisition device 510 with respect to track assembly 512 in order to maintain speed of traversing of soil sample acquisition device 510 with respect to the soil equal to zero equals, of course, true ground speed of the vehicle; i.e., wheel speed less any wheel slippage which may occur under heavy draft conditions or in wet soil. A true ground speed signal is preferably obtained from ground speed sensor 134 (i.e., a radar system with antenna located near and oriented toward the surface of the soil), and sent through bus 640 to soil sample module 520 for use in track actuator, or probe traverse, module 540 in controlling traverse speed of soil sample acquisition device 510.

Position feedback of soil sample acquisition device 510 with respect to track assembly 512 is needed only at the ends of track assembly 512, to control on/off and direction of the track actuator. Plunging of soil engaging portion 518 is not initiated by a sample acquire module 560 unless sample acquire module 560 receives a signal indicating that soil sample acquiring device 510 is at the forward end of track assembly 512. Position feedback may be obtained from an optical or magnetic encoder mounted upon the shaft of the track actuator, from encoding of the surface itself of the belt or of the track, or from limit switches located near the ends of track assembly 512. Since cycling speed of the soil sampling system 500 must be reasonably fast to accommodate small sampling site grid pitches, traverse speed of the soil sample acquisition device 510 on the return stroke must be similarly fast. To minimize shock at the end of the traverse return stroke, deceleration of the sample acquisition device 510 may be implemented by use of a deceleration subroutine in the probe traverse module 540 and/or by use of snubbers (e.g., a biasing device such as a compression spring or a small hydraulic shock absorber provided with its own return spring).

Alternatively, however, analysis of soil constituents may be done on or about the vehicle substantially in real time by either (a) an analyzing device or sensor in contact with the soil and both analyzing the soil and communicating data on a continuous basis or (b) a device which analyzes discrete samples of soil, as does the off-line system above, but with associated core unit 102 transmitting analysis data to a remote memory device 114 while the field operation is in progress. Analyzing devices available for (a) and (b) above include samples with identifying labels can be sent to a soil lab for analysis with the resulting data entered into the data base from the office computer. Development for real time soil sensors is underway at many universities and when these products become available they can be integrated into the sample retrieval and data logging devices. In that case the sample data can be recorded without the need for collecting samples which may reduce or eliminate the requirement for a labs analysis.

While the embodiments illustrated in the Figures and described above are presently preferred, it should be understood that these embodiments are offered by way of example only. For example, voice-communication interface 126 can be used to generate command signals instead of switches 124 to further simplify the operator interface by allowing an operator to issue a command by speaking its name (e.g., "Apply."). Samples need not be physically removed from the soil if the sample acquiring apparatus is configured to analyze samples in place. The invention is not intended to be limited to any particular embodiment, but is intended to extend to various modifications that nevertheless fall within the scope and spirit of the appended claims.

What is claimed is:

1. An agricultural system for the acquiring of soil samples from a field of land, the system comprising:

vehicle movable across the field and including an implement configured to perform at least one agricultural operation while in motion;

a soil sample acquiring apparatus supported by the vehicle and configured to acquire samples of soil from the field while the vehicle is in motion, wherein the soil sample acquiring apparatus includes a longitudinal track assembly and a soil sample acquisition device, the longitudinal track assembly configured to cause the soil sample acquisition device to move in a direction opposite to the direction of motion of the vehicle when the soil sample acquisition device is engaged in the soil, whereby relative motion between the soil sample acquisition device and the field is substantially zero;

a location signal generating circuit supported by the vehicle configured to generate location signals, each location signal corresponding to one sample acquired location within the field; and a data recorder supported by the vehicle and configured to record the location signals.

2. The system of claim 1, further comprising:

an apparatus supported by the vehicle for placing each sample into an individual container, which container may be connected to another individual container; and an apparatus supported by the vehicle configured to apply a unique identification upon each individual sample container.

3. The system of claim 2, wherein the unique identification is an alphanumeric indicia which is incremented for each sample, the system further comprising:

a memory device supported by the vehicle; and a control circuit supported by the vehicle and connected to the location signal generating circuit and to the memory, and configured to correlate each sample designation with the corresponding locational data to form a data set and to store the correlated data sets in the memory device, wherein each sample acquired is correlated to its location within the field direct and independent of any other sample acquired.

4. The system of claim 3 wherein the memory device is portable and configured for uploading to a data base in a remote data processing apparatus for off line analysis of the soil samples.

5. The system of claim 4 wherein the data base is a geographic information system (GIS) and the location signal generating circuit is a global positioning system (GPS) which may be provided with an associated differential global positioning system (DGPS).

6. The system of claim 5 wherein each sample designation is applied to the corresponding container as a bar code.

7. The system of claim 2 wherein the unique identification is the sample source locational description and is applied to the corresponding container as a bar code.

8. The system of claim 7 wherein the location signal and unique identification corresponding to each sample are correlated into a data set and stored in a geographic information system (GIS) data base and the location signal generating circuit is a global positioning system (GPS) which may be provided with an associated differential global position system (DGPS).

9. The system of claim 1, further comprising:

a memory device;

an apparatus supported by the vehicle for analyzing the soil samples at the vehicle in real time; and a control circuit connected to the location signal generating circuit and the soil sample analyzing apparatus, configured to cause the analyzer to analyze the soil samples, correlate the analyses data with the corresponding locational data, and store the correlated data sets in the memory device.

10. The system of claim 9 wherein the memory device is portable and configured to upload data off line to a data base located in a remote data processing apparatus.

11. The system of claim 10 wherein the data base is a geographic information system (GIS) program and the location signal generating circuit is a global positioning system (GPS) configured to generate GPS signals which may be provided with an associated differential global positioning system (DGPS) configured to generate GPS differential correction signals, wherein the location signals include GPS signals modified by GPS differential correction signals to increase location accuracy.

12. The system of claim 9 wherein the memory device is located remotely and may be in communication with the vehicle-supported control circuit through a wireless data link, the control circuit being configured to upload the correlated data sets to the remote memory device.

13. The system of claim 12 further comprising a plurality of vehicles which are so equipped whereby they may upload data through a communication network in real time and substantially concurrently to the remote memory device.

14. The system of claim 13 wherein the correlated data sets are included in a geographic information system (GIS) data base and the location signal generating circuit is a global positioning system (GPS) configured to generate GPS signals, which may be provided with an associated differential global positioning system (DGPS) configured to generate GPS differential correction signals, wherein the location signals include GPS signals modified by GPS differential correction signals to increase location accuracy.

15. The system of claim 12 wherein the vehicle-supported control circuit and the remote memory device are configured for two-way communication, whereby the vehicle may upload data to the remote memory device in real time and the remote memory device may download prescriptive map data, and other data as desired, to the vehicle.

16. The system of claim 15 further comprising a plurality of vehicles which are so equipped whereby they may exchange data through a communications network in real time and substantially concurrently with the remote memory device and with each other.

17. The system of claim 16 wherein the correlated data sets are included in a geographic information system (GIS) program and the location signal generating circuit is a global positioning system (GPS) which may be provided with an associated differential global positioning system (DGPS).

18. A method for acquiring a plurality of soil samples from an agricultural field of land while work is being performed on the field by a work vehicle moving over the field, the vehicle including an agricultural implement, the method comprising the steps of:

(a) acquiring samples of the soil utilizing a soil sample acquiring apparatus, the apparatus including a longitudinal track assembly and a sample acquiring device, the device movably supported to the vehicle by the longitudinal track assembly whereby the device remains stationary with respect to the soil while the sample is acquired;

(b) receiving location signals;

(c) processing the location signals in a control circuit supported by the vehicle to generate location data representative of the plurality of locations; and (d) recording the location data.

19. The method of claim 18, further comprising the steps of:

(e) placing each soil sample into an individual container, which containers may be connected to each other; and (f) uniquely identifying each container.

20. The method of claim 19 wherein the unique identification is an alphanumeric indicia which is incremented for each sample and is applied to the corresponding container, the method further comprising the steps of:

(g) correlating each unique identification with the corresponding locational data, wherein each sample acquired is correlated to its location within the field direct and independent of any other sample acquired; and (h) storing the correlated data sets in a memory device supported by the vehicle.

21. The method of claim 20 wherein the memory device is portable, the method further comprising steps of:

(i) transferring the correlated unique identification and locational data from the portable memory device into a data base in a remote data processing apparatus; and (j) scanning the unique identification indicia bar coded upon the container into the data processing apparatus to facilitate correlating of the corresponding off line sample analysis data.

22. The method of claim 21 wherein the data base is a geographic information system (GIS) program and the location signals are received from a global positioning system (GPS) which may be provided with an associated differential global positioning system (DGPS).

23. The method of claim 21 wherein each unique identification is applied to the container as a bar code.

24. The method of claim 19 wherein step (f) of uniquely identifying each container includes an unique sample identification having a sample source location description, the method further comprising the steps of:

(g) applying each unique sample identification to the corresponding container as a bar code; and (h) scanning each bar coded unique sample identification into a data base in a remote data processing apparatus.

25. The method of claim 24 wherein the data base is a geographic information system (GIS) and the location signals are received from a global positioning system (GPS) which may be provided with an associated differential global positioning system (DGPS).

26. The method of claim 19, further comprising the steps of:

(e) analyzing the soil samples at the vehicle to produce soil data in real time;

(f) correlating each sample's soil data with the corresponding locational data to form data sets;

(g) storing the data sets in a portable memory device supported by the vehicle; and (h) uploading the portable memory device off line to a data base in a remote data processing apparatus.

27. The method of claim 26 wherein the data base is a geographic information system (GIS) program and the location signal is received from a global positioning system (GPS) which may be provided an associated differential global positioning system (DGPS).

28. The method of claim 19, further comprising the steps of:
(e) analyzing the soil samples at the vehicle to produce soil data in real time;
(f) correlating each sample's soil data with the corresponding location data to form data sets; and
(g) uploading the data sets in real time via a wireless data link to a data base in a remote data processing apparatus, which data link may be additionally used to download prescriptive map data, and other information as desired, from the remote data processing apparatus to the control circuit supported by the vehicle.

29. The method of claim 28 wherein the data base is a geographic information system (GIS) program and the location signal is received from a global positioning system (GPS) which may be provided an associated differential global positioning system (DGPS).

30. The method of claim 29, further comprising the step of:
(h) communicating soil and location data, and other information as desired, through a communications network by a plurality of vehicles with the remote data processing apparatus and with each other in real time and substantially concurrently.

* * * * *